United States Patent [19]
Hardy et al.

[11] Patent Number: 5,599,969
[45] Date of Patent: Feb. 4, 1997

[54] PROCESS OF RESOLVING PHENYLPROPIONIC ACIDS USING α-METHYLBENZYLAMINE

[75] Inventors: Robert Hardy; Paul F. Coe; Adrian Hirst; Hugh O. O'Donnell, all of Nottingham, England

[73] Assignee: The Boots Company PLC, Nottingham, England

[21] Appl. No.: 424,517

[22] PCT Filed: Nov. 30, 1993

[86] PCT No.: PCT/EP93/03376

§ 371 Date: Jun. 21, 1995

§ 102(e) Date: Jun. 21, 1995

[87] PCT Pub. No.: WO94/12460

PCT Pub. Date: Jun. 9, 1994

[30] Foreign Application Priority Data

Dec. 2, 1992 [GB] United Kingdom ............ 9225202
Dec. 2, 1992 [GB] United Kingdom ............ 9225203

[51] Int. Cl.$^6$ ............................................. C07B 57/00
[52] U.S. Cl. ............................................. 562/401
[58] Field of Search .......................... 562/401, 402

[56] References Cited

U.S. PATENT DOCUMENTS

| | | | |
|---|---|---|---|
| 4,994,604 | 2/1991 | Tung | 562/401 |
| 5,015,764 | 5/1991 | Manimaran | 562/401 |
| 5,200,558 | 4/1993 | Kwan | 562/496 |
| 5,248,813 | 9/1993 | Manimaran | 562/401 |
| 5,260,482 | 11/1993 | Pringle | 562/401 |
| 5,278,337 | 1/1994 | Manimaran et al. | 562/401 |

FOREIGN PATENT DOCUMENTS

| | | |
|---|---|---|
| 55092/90 | 11/1990 | Australia . |
| 362476 | 4/1990 | European Pat. Off. . |
| 437369 | 1/1991 | European Pat. Off. . |
| 424028 | 4/1991 | European Pat. Off. . |
| 486046 | 5/1992 | European Pat. Off. . |
| 486045 | 5/1992 | European Pat. Off. . |
| 505180 | 9/1992 | European Pat. Off. . |
| 1471910 | 4/1977 | United Kingdom . |
| 1497044 | 1/1978 | United Kingdom . |
| 92/04018 | 5/1991 | WIPO . |
| 92/20334 | 11/1992 | WIPO . |
| 93/13770 | 1/1993 | WIPO . |
| 94/03209 | 7/1993 | WIPO . |
| 93/14056 | 7/1993 | WIPO . |
| 94/03188 | 7/1993 | WIPO . |
| 94/07471 | 9/1993 | WIPO . |

OTHER PUBLICATIONS

Collet, Optical resolution by crystallization methods, in Chiral Separations by HPLC, Krstulovic, 1989.
Gabard et al, Nouveau Journal de Chim, 10(12), 1986, pp. 685–690.
Jacques et al, Enantiomers, Racemates and Resolutions, Wiley, 1981, pp. 423–434.
Collet et al, Optical Resolution by Direct Crystallization of Enantiomer Mixtures, Chemical Reviews, 80(3), 1980, pp. 215–230.
Patent abstracts of Japan 5(8) 20 Jan. 1981 (c–39) (680) and JP, A, 55136245 20 Oct. 1980.

*Primary Examiner*—Gary Geist
*Assistant Examiner*—Samuel Barts
*Attorney, Agent, or Firm*—Nikaido, Marmelstein, Murray & Oram LLP

[57] ABSTRACT

A process for the production of a product which is enriched in a desired enantiomer of a phenylpropionic acid selected from ibuprofen and flurbiprofen, or their pharmaceutically acceptable salts, which comprises a resolution stage, a recrystallization stage, an optional liberation stage, and an optional salt preparation stage. A substantially racemic mixture of the phenylpropionic acid is contacted with an enantiomer of α-methylbenzylamine, in specific ratios, to produce the enantiomerically enriched product.

29 Claims, 1 Drawing Sheet 5,599,969

PROCESS OF RESOLVING PHENYLPROPIONIC ACIDS USING α-METHYLBENZYLAMINE

This application is a 371 of PCT/EP93/03376 filed Nov. 30, 1993.

FIELD OF THE INVENTION

The present invention relates to the production of substantially pure enantiomers of phenylpropionic acids selected from ibuprofen, flurbiprofen and pharmaceutically acceptable salts thereof, in particular their α-methylbenzylamine, lysine and sodium salts.

DESCRIPTION OF THE RELATED ART

Ibuprofen, the chemical name of which is 2-(4-isobutylphenyl)propionic acid and flurbiprofen, the chemical name of which is 2-(2-fluoro-4-biphenylyl)propionic acid are well known medicaments with anti-inflammatory, antipyretic and analgesic activities. Known uses of ibuprofen and flurbiprofen include the treatment of pain and inflammation in musculoskeletal disorders such as rheumatic disease, and the treatment of pain in a variety of other disorders, for example headache, neuralgia and dysmenorrhoea.

Both ibuprofen and flurbiprofen contain a single chiral centre at an asymmetrically substituted carbon atom and therefore both exist in two enantiomeric forms. It is known that S(+)-ibuprofen is the active agent and that R(−)-ibuprofen may be incompletely converted into S(+)-ibuprofen in humans. It is also known that S(+)-flurbiprofen is the active agent. R(−)-flurbiprofen is not converted into the (S)-enantiomer in humans, although it has been suggested that R(−)-flurbiprofen has analgesic activity only (international patent application WO 92/04018 [Paz]). Ibuprofen and flurbiprofen have been marketed previously as the racemic mixture. However in certain circumstances it may be advantageous to administer substantially one enantiomer only. Therefore it is desirable to provide improved processes for production of a product enriched in a desired enantiomer of a phenylpropionic acid selected from ibuprofen and flurbiprofen.

European Patent Application 0362476 (Paz) describes the separation of enantiomeric forms of aryl propionic acids by selective crystallisation of a diastereomeric salt in a polar solvent. Use of polar solvents are stated to be more favourable than apolar solvents, which teaches away from using the specific solvent mixture in the process of the present invention.

U.S. Pat. No. 5,015,764 (Manimaran) relates to the preparation of aliphatic carboxylic acids including ibuprofen and flurbiprofen by treating a solution of their salts with a chiral organic base to selectively precipitate the less soluble diastereoisomer. There is no disclosure of the use of the specific solvent mixture used in the process of the present invention.

European Patent Application 0437369 describes the preparation of (S)-ibuprofen-(S)-lysine salts by contacting racemic ibuprofen with an equimolar amount of (S)-lysine in an aqueous organic solvent mixture, separating any suspended solid from the mixture, cooling the clear mixture until it is supersaturated with respect to both the (R)-ibuprofen-(S)-lysine and the (S)-ibuprofen-(S)-lysine salts, contacting the supersaturated solution with a slurry of (S)-ibuprofen-(S)-lysine salt and separating the formed crystalline S-ibuprofen-(S)-lysine salt.

International Patent Application WO 92/20334 Boots) describes the preparation of the sodium salt of (S)-ibuprofen.

SUMMARY OF THE INVENTION

The present invention provides a process for the production of a product which is enriched in a desired enantiomer of a phenylpropionic acid selected from ibuprofen and flurbiprofen which comprises the following stages:

(a) a resolution stage, in which an α-methylbenzylamine salt of the phenylpropionic acid is prepared which is enriched in the desired enantiomer by contacting, in a mixture of toluene and methanol as solvent, a substantially racemic mixture of the phenylpropionic acid with an enantiomer of α-methylbenzylamine, the respective molar ratio of the substantially racemic phenylpropionic acid to the α-methylbenzylamine being in the range of about 1:0.25 to about 1:1;

b) a recrystallization stage, in which the resulting enriched salt is recrystallised from a mixture of methanol and toluene to give an α-methylbenzylamine salt of the phenylpropionic acid which is further enriched in the desired enantiomer;

c) an optional liberation stage, in which the phenylpropionic acid which is further enriched in the desired enantiomer is liberated from the recrystallised salt.

d) an optional salt-preparation stage in which a solid salt of the phenylpropionic acid further enriched in the desired enantiomer is isolated, the solid salt optionally being even further enantiomerically enriched in the desired enantiomer.

DESCRIPTION OF THE PREFERRED EMBODIMENTS

Figure 1:
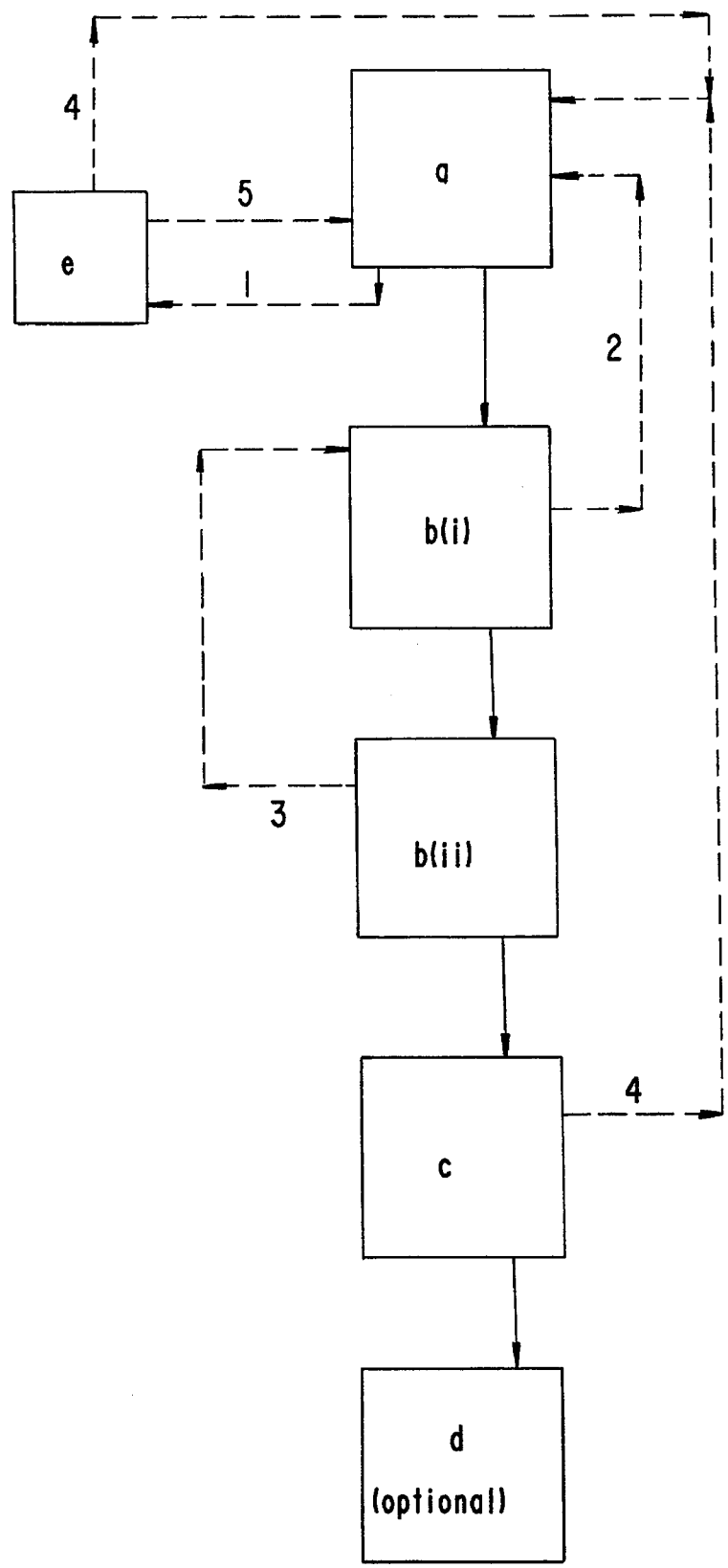
FIG. 1 is a diagrammatic flowchart of the process of the present invention.

In preferred embodiments of the process of the present invention, the desired enantiomer of the phenylpropionic acid is the (S)-enantiomer and:

a) in the resolution stage, the substantially racemic phenylpropionic acid and (S)-α-methylbenzylamine are used in a respective molar ratio of about 1:0.35 to about 1:0.8, for example about 1:0.4 to about 1:0.6 and the preparation takes place in a mixture of methanol and toluene, in which the toluene comprises at least about 50%, more preferably from about 60% to about 90%, most preferably from about 70% to about 80%, of the total mixture by volume; the temperature of the mixture is in the range from about 30° C. to about 70° C., preferably from about 40° C. to about 60° C., to form a supersaturated solution; from which a phenylpropionic acid -(S)-α-methylbenzylamine salt enriched in the (S)-enantiomer of the phenylpropionic acid is crystallised, for example when the solution is cooled to a temperature in the range from about −10° C. to about 30° C., preferably from about 0° C. to about 5° C.;

(b) in the recrystallisation stage the preferred solvent is a mixture of methanol and toluene in which the toluene comprises at least about 25%, more preferably from about 50% to about 80%, most preferably from about 60% to about 70%, of the total mixture by volume; from which a phenylpropionic acid -(S)-α-methylbenzylamine salt further enriched in the (S)-enantiomer of the phenylpropionic acid is crystallised, for example when the solution is cooled to a temperature in the range from about −10° C. to about 30° C., preferably from about 0° C. to about 5° C.;

(c) in the liberation stage the (S)-α-methylbenzylamine salt of further-(S)-enriched-phenylpropionic acid, obtained from the recrystallisation stage, is acidified (for example with hydrochloric acid) in a water-immiscible solvent to produce a solution of liberated (S)-enriched-phenylpropionic acid in the water-immiscible solvent and an aqueous solution of a salt of (S)-α-methylbenzylamine (for example, the hydrochloride salt) from which (S)-α-methylbenzylamine can be liberated so that it can be reused in a subsequent resolution stage (a), for example by basifying the solution and extracting the liberated base into toluene;

(d) optionally in the salt-preparation stage the solution of further-(S)-enriched-phenylpropionic acid in the water-immiscible solvent obtained from the liberation stage (c) may be further processed by one or more of the following methods:

(i) crystallisation and isolation of the solid (S)-enriched-phenylpropionic acid from the solution;

(ii) removal of the solvent by distillation to give a melt which can be used in step (v) below;

(iii) where the phenylpropionic acid is ibuprofen, contact with an aqueous solution of a sodium-containing base (e.g. sodium hydroxide) to produce an aqueous solution of the sodium salt of ibuprofen, which is separated from the water-immiscible solvent, the aqueous solution then being diluted with acetone to crystallise further-(S)-enriched-sodium-ibuprofen; and (iv) where the phenylpropionic acid is ibuprofen, contact with (S)-lysine and water in which the respective molar ratio of ibuprofen to (S)-lysine is in the range 1:0.5 to 1:1 to give an aqueous solution of the (S)-lysine salt which is separated from the immiscible solvent, ethanol then being added to the aqueous solution to crystallise further-(S)-enriched-ibuprofen-(S)-lysine. The product of steps d(i) to d(iii) above may be used in one or more of the following further steps:

(v) the solid from step d(i) above or the melt from step d(ii) which is separated and reacted in an aqueous ethanolic solution with (S)-lysine in which the molar ratio of the phenylpropionic acid to (S)-lysine is in the range 1:0.5 to 1:1, to give, after crystallisation and separation, an (S)-lysine salt of the further-(S)-enriched-phenylpropionic acid;

(vi) acidification of the further-(S)-enriched-sodium ibuprofen from step d(iii) above in the presence of a water immiscible solvent, such as heptane, to produce a solution of further-(S)-enriched ibuprofen in the water-immiscible solvent which is separated. Solid (S)-enriched-ibuprofen is then crystallised and isolated; and (vii) acidification of the aqueous solution of the further-S-enriched-sodium-ibuprofen from d(iii) above at elevated temperature (for example at 60° C.) to give a melt which is separated from the aqueous layer and treated as described in (v) above.

In more preferred embodiments of the process of the present invention the phenylpropionic acid is ibuprofen and the desired enantiomer is the (S)-enantiomer. In this more preferred embodiment:

(a) the resolution stage produces a (S)-α-methylbenzylamine salt of (S)-enriched ibuprofen of an enantiomeric purity from about 80% to about 95% by weight, and a first mother liquor comprising (R)-enriched-ibuprofen, which is used in a racemisation stage (e) to produce substantially racemic ibuprofen which is introduced as part of the starting material used in a subsequent resolution stage (a);

(b) the recrystallisation stage comprises two steps:

(i) a first recrystallisation step comprising recrystallising the (S)-enriched-ibuprofen-(S)-α-methylbenzylamine produced from the resolution stage (a) , to produce (S)-enriched-ibuprofen-(S)-methylbenzylamine preferably of an enantiomeric purity from about 90% to about 99.9%, more preferably from about 94% to about 99%, by weight, and a second mother liquor comprising (S)-enriched ibuprofen-(S)-α-methylbenzylamine of an enantiomeric purity from about 40% to about 70%, more preferably from about 40% to about 60% by weight, the second mother liquor being introduced as part of the solvent used in a subsequent resolution step (a); and (ii) a second recrystallisation step comprising recrystallisation of the (S)-enriched-ibuprofen-(S)-α-methylbenzylamine produced from the first recrystallisation step (b) (i) to produce substantially enantiomerically pure (S)-ibuprofen-(S)-α-methylbenzylamine, preferably of an enantiomer purity of about 99%, and a third mother liquor comprising (S)-enriched-ibuprofen-(S)-α-methylbenzylamine of an enantiomeric purity from about 85% to about 95% by weight, preferably from about 88% to about 95% by weight, the third mother liquor being introduced as part of the solvent used in into a subsequent first recrystallisation step (b) (i).

In a most preferred embodiment of the invention, the first mother liquor from the resolution stage (a) is subjected to azeotropic distillation to remove substantially all the methanol at temperatures which avoid substantially the formation of by-products, the distillate being reused as part of the solvent in a subsequent resolution stage (a). The residue remaining after the distillation above may be acidified, with for example hydrochloric acid, to give an aqueous solution of a (S)-α-methylbenzylamine salt, for example (S)-α-methylbenzylamine hydrochloride, and an organic phase comprising (R)-enriched ibuprofen. The aqueous solution is then separated and basified to give free (S)-α-methylbenzylamine which is extracted into toluene and reused as the resolving agent at the start of a subsequent resolution stage (a) along with (S)-α-methylbenzylamine recovered in the liberation stage(s). The organic phase comprising (R)-enriched-ibuprofen may be racemised in a racemisation stage (e) by any known method to produce substantially racemic ibuprofen which may then be introduced as part of the solvent used at the start of a subsequent resolution stage (a).

Preferably at each stage of the process of the present invention liquors not comprising the phenylpropionic acid enriched in the desired enantiomer may be recycled by using them in previous stages of the process. Combining the resolution stage (a) and recrystallisation stage (b) with a racemisation stage (e) and a recovery stage for the (S)-α-methylbenzylamine resolving agent has the advantage of avoiding treatment of multiple streams of liquors produced from each stage and reduces the production cost by saving time, energy and raw materials.

Optionally the recrystallisation stage in the process described above may include a third and/or subsequent recrystallisation step.

This preferred combined process is illustrated by reference to the drawing in which FIG. 1 is a diagrammatic flow chart of a preferred process of the invention for production of (S)-ibuprofen in which the letters refer to the stages or steps labelled (a), (b)(i), (b)(ii), (c), (d) and (e) in the above described processes and; the numbers 1 to 3 indicate the first to third mother liquors respectively, the number 4 indicates the recycled (S)-α-methylbenzylamine and the number 5 indicates the recycled racemised ibuprofen. In FIG. 1, dotted lines indicate recycled materials and solid lines indicates material increasing in enrichment of (S)-ibuprofen in the direction of the arrow.

Resolution stage (a) yields an (S)-enriched-ibuprofen-(S)-α-methylbenzylamine product which is used as the starting material for the first recrystallisation step (b) (i). The first mother liquors (1) from the resolution stage (a) pass to a racemisation stage (e) from which racemic ibuprofen (5) is recycled to form part of the starting material for a subsequent resolution stage (a) and recovered (S)-α-methylbenzylamine (4) is recycled to be used as part of the resolving agent for a subsequent resolution stage (a). The second mother liquors (2) from the first recrystallisation step (b)(i) are recycled for use in a subsequent resolution step (a). The product of the first recrystallisation step (b)(i) undergoes a second recrystallisation step (b)(ii) to give (S)-ibuprofen-(S)-α-methylbenzylamine of increased enantiomeric purity and a third mother liquor which is recycled to form part of the solvent used in a subsequent first recrystallisation step (b)(i). The product from the second recrystallisation step (b)(ii) is then used in a liberation stage (c) to give (S)-ibuprofen of high enantiomeric purity. (S)-α-Methylbenzylamine (4) which is also liberated in the liberation stage (c) is recycled to be used as part of the resolving agent for a subsequent resolution stage (a). The liberated (S)-ibuprofen may then be used in an optional salt-preparation stage (d) to form salts (for example the sodium or (S)-lysine salt) containing (S)-ibuprofen of even higher enantiomeric purity.

A product of the above processes, when the phenylpropionic acid is ibuprofen and the desired enantiomer is the (S)-enantiomer, may be used to prepare a (S)-lysine salt of (S)-enriched ibuprofen by contacting the liberated (S)-enriched- ibuprofen with (S)-lysine, preferably with a stoichiometric amount or less of (S)-lysine to produce a (S)-lysine salt of further-(S)-enriched-ibuprofen, more preferably the molar ratio of ibuprofen to (S)-lysine being in the range from about 1:0.5 to about 1:1 preferably about 1:0.5 to about 1:0.95. The liberated (S)-enriched-ibuprofen can also be contacted with sodium hydroxide to produce further-(S)-enriched sodium ibuprofen (see for example International Patent Application WO 92/20334).

In a further preferred embodiment the process of the present invention gives (S)-ibuprofen, and salts thereof, of high enantiomeric purity.

Surprisingly it has also been found that (S)-enriched-flurbiprofen may be crystallised from toluene with the efficient removal of the other enantiomer to give (S)-flurbiprofen of a high enantiomeric purity.

It will be readily understood that if the production of R(–)-ibuprofen, R(–)-flurbiprofen or their pharmaceutically acceptable salts is desired, the above processes can be readily adapted for production of the R(–)-ibuprofen, R(–)-flurbiprofen or their pharmaceutically acceptable salts by substituting (R)-α-methylbenzylamine for (S)-α-methylbenzylamine as the resolving agent in the resolution stage (a) of the processes of the present invention, with corresponding modifications to the subsequent stages.

The invention will now be illustrated by the following Examples.

Example 1

Resolution of Ibuprofen by Preparation of (S)-Enriched-Ibuprofen-(S)-α-Methylbenzylamine [Resolution Stage (a)]

Recycled racemic ibuprofen (530 kg) was dissolved in toluene (1335 l) and methanol (900 l) was added and the mixture was heated with stirring to 66° C. Recycled (S)-α-methylbenzylamine (247 kg) in toluene (200 l) was added over 3 hours whilst the temperature was maintained in the range 65°–70° C. The mixture was cooled finally to 0° to 5° C. with stirring and stirred at this temperature for one hour. The desired product was collected by filtration, washed with toluene (600 l). The product contained (S)-α-methylbenzylamine salt of (S)-enriched-ibuprofen of an enantiomeric purity of 89.3% by weight. The mother liquors were retained for processing in a similar manner to that described in Example 6.

Example 2

Recrystallisation Stage of the (S)-α-Methylbenzylamine Salt of (S)-Enriched Ibuprofen [Recrystallisation Stage (b)]

Example 2(a) [First Recrystallisation Step (b)(i)]

(S)-enriched-ibuprofen-(S)-α-methylbenzylamine (635 kg) of an enantiomeric purity of 85.5% by weight, obtained in a similar manner to that described in Example 1 above), toluene (598 l) and recycled second mother liquor (2350 l, obtained from Example B2 below, comprising (S)-enriched-ibuprofen-(S)-α-methylbenzylamine (214 kg) and methanol (800 l) stirred, heated and dissolved at 67° C. and then cooled finally a temperature in the range of 0° C. to 5° C. The resulting solid was collected by filtration. The product was (S)-enriched-ibuprofen-(S)-α-methylbenzylamine of an enantiomeric purity of 94.1% by weight.

Example 2(b) [Second Recrystallisation Step (b)(ii)]

In a similar manner to the first recrystallisation step described in Example 2(a) above, the (S)-enriched-ibuprofen-(S)-α-methylbenzylamine of an enantiomeric purity of 91.4% by weight (629 kg, obtained in a similar manner to that described in Example 2(a) above) was recrystallised from a mixture of toluene (115 l), and washed with toluene (200 l) so that it had an enantiomeric purity of 98.5% by weight.

Examples 2(a) and 2(b) illustrate that a substantial upgrading in the enantiomeric purity of (S)-enriched-ibuprofen-(S)-α-methylbenzylamine can be achieved at the recrystallisation stage in the process of the present invention.

Example 3(a)

Liberation of (S)-Enriched Ibuprofen in Toluene Solution [Liberation Stage (c)]

The (S)-enriched-ibuprofen-(S) -α-methylbenzylamine salt (485 kg, prepared as described in Example 2(b) above), toluene (814 l), water (300 l) and concentrated hydrochloric acid of specific gravity 1.18 (170 kg) was stirred for 30 minutes. The lower aqueous layer comprising (S)-α-methylbenzylamine hydrochloride was separated, combined with the aqueous liquors as described in Example 6 below before being recycled as described in Example 1 above. The upper layer comprising a toluene solution of (S)-enriched-ibuprofen was washed with water (100 l) to give 920 kg of a solution containing 300 kg of (S)-enriched-ibuprofen of enantiomeric purity of 98.5% by weight.

Example 3(b)

Purification of (S)-Enriched Ibuprofen

A solution of (S)-enriched ibuprofen having an enantiomeric purity of 98.2% (180 kg) in toluene (1221 kg) was washed with water. Water (220 l) and aqueous sodium hydroxide solution (47 l—specific gravity 1.5) were added and the mixture heated to 60° C. and allowed to settle for four hours. The lower aqueous layer was separated and the toluene layer washed with water. The aqueous washing was combined with the aqueous layer. Residual toluene was removed by distillation and heptane (250 l) and the concentrated hydrochloric acid (78 kg—specific gravity 1:18) were added. The heptane layer was separated, washed with water and cooled to −10° C. (S)-Enriched ibuprofen having an enantiomeric purity of greater than 99% was collected by filtration and dried in vacuo. (Yield 166 kg).

Example 4(a)

Preparation of (S-Enriched Ibuprofen-(S)-Lysine [Salt Preparation Stage (d)]

Examples 4.1 to 4.12 were performed as described below with reference to Table 1. Ibuprofen enriched in the (S)-enantiomer (100 g of a material containing 'a'% of the (S)-enantiomer) was dissolved in ethanol (900 ml) at ambient temperature. A solution of (S)-lysine monohydrate ('b' g) in a mixture of water ('c' ml) and ethanol ('d' ml) was prepared. The ibuprofen solution and the (S)-lysine solution were added simultaneously at equimolar rates over a period of one hour to a suspension of (S)-ibuprofen-(S)-lysine salt (9.5 g) in water (11 ml) and ethanol (125 ml) which had been stirred at 20° C. for 10 minutes. The mixture was then cooled to 0° C. over one hour and then cooled to −10° C. The mixture was stirred at −10° C. for two hours. The resulting solid was collected by filtration, washed with ethyl acetate and dried in vacuo at 35° C. to give (S)-enriched-ibuprofen-(S)-lysine salt of an enantiomeric purity of 'e'% by weight.

TABLE 1

| Example | a | b | c | d | e |
|---------|-------|------|------|----|------|
| 4.1 | 94.54 | 60.3 | 79 | 55 | 98.9 |
| 4.2 | 99.16 | 60.3 | 79 | 55 | 99.8 |
| 4.3 | 91.1 | 60.3 | 79 | 55 | 98.4 |
| 4.4 | 94.54 | 67.5 | 85.5 | 55 | 98.7 |
| 4.5 | 94.54 | 64 | 82 | 55 | 98.6 |
| 4.6 | 91.1 | 67.5 | 85.5 | 55 | 97.8 |
| 4.7 | 99.16 | 64 | 82 | 55 | 99.7 |
| 4.8 | 99.16 | 67.5 | 85.5 | 55 | 99.7 |
| 4.9 | 91.1 | 64 | 82 | 55 | 97.8 |
| 4.10 | 94.54 | 60.3 | 79 | 55 | 98.5 |
| 4.11 | 94.54 | 64 | 82 | 55 | 98.6 |
| 4.12 | 99.16 | 67.5 | 85.5 | 55 | 99.7 |

Examples 4.1 to 4.12 illustrate that a substantial upgrading in the enantiomeric purity of (S)-enriched-ibuprofen-(S)-lysine salt can be achieved at the preparation stage in the process of the present invention.

Example 4

Preparation of S-Enriched-Ibuprofen-(S)-Lysine (Salt Preparation Stage (d))

A solution of (S)-enriched ibuprofen (30 g) in toluene (20 g) was heated at 60° to 70° C. with (S)-lysine (40 g of a 50% w/w aqueous solution) and water (20 ml). The lower aqueous layer was separated and residual solvent removed by distillation. Ethanol (460 ml) was added and the mixture heated to 50° to 55° C. and then cooled to 0° C. to −10° C. for thirty minutes. Crystalline (S)-enriched-ibuprofen-(S)-lysine was collected, washed with ethyl acetate (50 ml) and dried in vacuo.

Example 5

Preparation of (S)-Enriched Ibuprofen Sodium Salt [Salt Preparation Stage (d)]

A solution of (S)-enriched ibuprofen having an enantiomeric purity of 95.5% (211 kg) in toluene (797 kg) was heated to 60° C. with water (300 l) and aqueous sodium hydroxide solution (52 l—specific gravity 1.5) and allowed to settle for four hours. The aqueous layer was separated and the toluene layer washed with water. The aqueous washings and the aqueous layer were combined and residual toluene removed by distillation. Acetone (1684 kg) was added and the mixture cooled to 20° C. The sodium salt of (S)-enriched ibuprofen dihydrate (having an enantiomeric purity of 99.9%) separated, was collected by filtration and dried in vacuo. (Yield 143.5 kg).

Example 6

Treatment of the First Mother Liquors From the Resolution Stage

A mixture of the first mother liquors from the resolution stage was concentrated by distillation to remove methanol and toluene for recovery and subsequent reuse. Water (300 l) and concentrated hydrochloric acid (170 kg—specific gravity 1.18) were added and the mixture stirred. The aqueous layer containing (S)-α-methylbenzylamine hydrochloride was separated and combined with the aqueous solution of (S)-α-methylbenzylamine hydrochloride from Example 3(a). The combined solutions were basified with aqueous sodium hydroxide solution (340 l—specific gravity 1.5). Toluene (500 l) was added and the resulting solution of (S)-α-methylbenzylamine used in a subsequent resolution stage performed in a similar manner to that described in Example 1.

Methanol (300 l) and concentrated sulphuric acid was heated under reflux for 2 hours. The upper organic layer was separated and heated under reflux with methanol (75 l) and concentrated sulphuric acid (15 l) for two hours. The upper layer was separated and heated with solid sodium hydroxide (175 kg). Methanol was removed by distillation and the residue acidified with a mixture of concentrated hydrochloric acid (353 kg) and water (1750 l). The upper toluene layer containing racemic ibuprofen was washed with water and used in the resolution stage of a subsequent preparation similar to that described in Example 1.

Example 7

Resolution of Flurbiprofen by Preparation of (S)-Enriched-Flurbiprofen-(S)-α-Methylbenzylamine Racemic flurbiprofen (61.0 g) was dissolved in a mixture of methanol (40 ml) and toluene (160 ml). The mixture was heated to 60° C. and (S)-α-methylbenzylamine 16.9 ml was added over 10 minutes. A seed crystal of (S)-flurbiprofen-(S)-α-methylbenzylamine was added to the reaction mixture which was then cooled to 0° to 5° C., and held at that temperature for one hour. The precipitate was collected by filtration to give a (S)-α-methylbenzylamine salt of (S)-enriched flurbiprofen-(S)-α-methylbenzylamine of an enantiomeric purity of 92.2%. After recrystallisation of the precipitate from a mixture of methanol (48 ml) and toluene (192 ml), a further-(S)-enriched-flurbiprofen-(S)-α-methylbenzylamine of an enantiomeric purity of 98.5% was obtained.

The mother liquor obtained from the recrystallisation was acidified with c. HCl (10 ml) and water (25 ml) and stirred at 25° C. for 15 minutes. The lower aqueous layer containing the (S)-α-methylbenzylamine was collected and reused. The upper organic layer contained a mixture of the flurbiprofen acid enantiomers in the weight ratio 41:5%:58.5%, S(+) to R(−) respectively. This flurbiprofen was transformed into its methylester which was racemised, converted back to racemic flurbiprofen with sodium hydroxide and reintroduced into the resolution step above.

Example 8

Preparation of (R)-Flurbiprofen-(R)-α-Methylbenzylamine

Examples 8.1 to 8.6 were performed below with reference to Table 2. Racemic flurbiprofen (i) g was dissolved in a mixture of methanol (ii) ml, and toluene (iii) ml and optionally water (iv) ml. The mixture was heated to 55° C. to form a solution and (R)-α-methylbenzylamine (v) ml was added over 10 minutes. A seed crystal of (R)-flurbiprofen-(R)-α-methylbenzylamine was added to the mixture which was cooled to 25° C. The precipitate was collected by filtration to give a (R)-α-methylbenzylamine salt of (R)-enriched-flurbiprofen of an enantiomeric purity of (vi)%. After recrystallisation of the precipitate from a mixture of methanol, toluene and water in the same ratio as used for the resolution stem, a solid was obtained of a further (R)-enriched-flurbiprofen-(R)-α-methylbenzylamine of an enantiomeric purity of (vii)%.

TABLE 2

| Ex | (i) Flurbiprofen/g | (ii) Methanol/ml | (iii) Toluene/ml | (iv) $H_2O$/ml | (v) MBA/ml | (vi) % enrichment | (vii) % enrichment |
| --- | --- | --- | --- | --- | --- | --- | --- |
| 8.1 | 61.0 g | 40.0 ml | 160 ml | — | 17 ml | 91.2% | 98.8% |
| 8.2 | 61.0 g | 70.0 ml | 280 ml | — | 17 ml | 92.0% | 99.3% |
| 8.3 | 61.0 g | 40.0 ml | 160 ml | — | 17 ml | 91.8% | 99.2% |
| 8.4 | 61.0 g | 40.0 ml | 160 ml | 10.0 ml | 17 ml | 92.4% | 99.1% |
| 8.5 | 61.0 g | 40.0 ml | 160 ml | 2 ml | 17 ml | 91.8% | 99.1% |
| 8.6 | 43.1 g | 20.0 ml | 180 ml | — | 12 ml | 91.9% | 99.1% |

Footnote:
1. A second recrystallisation in this example gave a further solid of (R)-enriched-flurbiprofen-(R)-α-methylbenzylamine of an enantiomeric purity greater than 99.9%

Example 9(a)

Liberation of (R)-Enriched Flurbiprofen (R)-Enriched-flurbiprofen-(R)-α-methylbenzylamine (58.7 g—prepared in a similar manner to that described in Example 8) having an enantiomeric purity of 99.1% was heated at 80° C. for 15 minutes with a mixture of n-heptane (160 ml), water (200 ml) and concentrated hydrochloric acid (17 ml—specific gravity 1.18). The organic layer was separated and cooled to 0° to 5° C. (R)-Enriched-flurbiprofen crystallised and was collected, washed with n-heptane and dried in vacuo.

Example 9(b)

Liberation of (S)-Enriched Flurbiprofen

In a similar manner to that described in Example 9(a), (S)-enriched-flurbiprofen is liberated from (S)-enriched-flurbiprofen-(S)-α-methylbenzylamine prepared in a similar manner to that described in Example 7.

Example 10(a)

Enantiomeric Purification of (S)-Enriched-Flurbiprofen by Recrystallisation (S)-enriched-flurbiprofen (47.2 g) of an enantiomer purity of 98.9% was added to toluene (132 ml) and heated to 50° C. Crystals of (S)-flurbiprofen were added with the temperature at 42° C. and the solution was cooled to −5° C. The solid (S)-enriched-flurbiprofen was collected by filtration and was found to have an enantiomeric purity of 99.8%.

Example 10(b)

Enantiomeric Purification of (S)-Enriched-Flurbiprofen by Recrystallisation (S)-enriched-flurbiprofen (13.5 g) of an enantiomer purity of 98.4% was added to toluene (26 ml) and heated to 50° C. The solution was then cooled to −10° C. The solid (S)-enriched-flurbiprofen was collected by filtration and was found to have an enantiomeric purity of 99.8%. Yield 13.0 g.

We claim:

1. A process for the production of a product which is enriched in a desired enantiomer of a phenylpropionic acid selected from ibuprofen or flurbiprofen which comprises the following stages:

(a) a resolution, in which an α-methylbenzylamine salt of the phenylpropionic acid is prepared which is enriched in the desired enantiomer by contacting, in a mixture of toluene and methanol as solvent, a substantially racemic mixture of the phenylpropionic acid with an enantiomer of α-methylbenzylamine, the respective molar ratio of the substantially racemic phenylpropionic acid to the α-methylbenzylamine being in the range of about 1:0.25 to about 1:1;

(b) a recrystallisation stage, in which the resulting enriched salt is recrystallised from a mixture of methanol and toluene to give an α-methylbenzylamine salt of the phenylpropionic acid which is further enriched in the desired enantiomer;

(c) an optional liberation stage, in which the phenylpropionic acid which is further enriched in the desired enantiomer is liberated from the recrystallised salt;

(d) an optional salt-preparation stage in which a solid salt of the phenylpropionic acid further enriched in the desired enantiomer is isolated, the solid salt optionally being even further enantiomerically enriched in the desired enantiomer;

(e) a racemisation stage, in which the phenylpropionic acid enriched in the undesired enantiomer is recovered from the first mother liquor of resolution stage (a), racemised, and the racemic phenylpropionic acid is reused in a subsequent resolution stage (a); and (f) a recovery stage for the α-methylbenzylamine resolving agent, in which α-methylbenzylamine is recovered from the first mother liquor of resolution stage (a) and optionally from the liberation stage (c) and is then reused in a subsequent resolution stage (a).

2. A process as claimed in claim 1, in which the desired enantiomer of the phenylpropionic acid is selected from (S)-ibuprofen, (S)-flurbiprofen and (R)-flurbiprofen.

3. A process as claimed in claim 1, in which the desired enantiomer of the phenylpropionic acid is the (S)-enantiomer and:

(a) in the resolution stage the substantially racemic phenylpropionic acid and (S)-α-methylbenzylamine are used in a respective molar ratio of about 1:0.35 to about 1:0.8, and the preparation takes place in a mixture of methanol and toluene, in which the toluene comprises at least about 50% of the total mixture by volume; the temperature of the mixture is in the range from about 30° C. to about 70° C., to form a supersaturated solution; from which a phenylpropionic acid-(S)-α-methylbenzylamine salt enriched in the (S)-enantiomer is crystallised;

(b) in the recrystallisation stage the solvent is a mixture of methanol and toluene, in which the toluene comprises at least about 25% of the total mixture by volume; from which a phenylpropionic acid-(S)-α-methylbenzylamine salt further enriched in the (S)-enantiomer of the phenylpropionic acid is crystallised;

(c) in the liberation stage the (S)-α-methylbenzylamine salt of further-(S)-enriched phenylpropionic acid, obtained from the recrystallisation stage, is acidified in a water-immiscible solvent to produce a solution of liberated (S)-enriched-phenylpropionic acid in the water immiscible solvent and an aqueous solution of a salt of (S)-α-methylbenzylamine from which the (S)-α-methylbenzylamine can be liberated so that it can be reused in a subsequent resolution stage (a).

4. A process as claimed in claim 3, in which:

(d) in the salt-preparation stage the solution of further-(S)-enriched-phenylpropionic acid in the water-immiscible solvent obtained from the liberation stage (c) may be further processed by one or more of the following methods:

(i) crystallisation and isolation of the solid (S)-enriched-phenylpropionic acid from the solution;

(ii) removal of the solvent by distillation to give a melt;

(iii) where the phenylpropionic acid is ibuprofen, contact with an aqueous solution of a sodium containing base to produce an aqueous solution of sodium ibuprofen which is separated from the water-immiscible solvent, the aqueous solution then being diluted with acetone to crystallise further-(S)-enriched-sodium-ibuprofen; or (iv) where the phenylpropionic acid is ibuprofen, contact with (S)-lysine and water in which the respective molar ratio of ibuprofen to (S)-lysine is in the range 1:0.5 to 1:1 to give an aqueous solution of the (S)-lysine salt which is separated from the immiscible solvent, ethanol then being added to the aqueous solution to crystallise further-(S)-enriched-ibuprofen-(S)-lysine.

5. A process as claimed in claim 4, which comprises a further salt-preparation step d(v), in which the solid from the salt-preparation step d(i) or the melt from the salt-preparation step d(ii) is separated and reacted in an aqueous ethanolic solution with (S)-lysine in which the respective molar ratio of the phenylpropionic acid to (S)-lysine is in the range of about 1:0.5 to about 1:1 to give, after crystallisation and separation, a (S)-lysine salt of the further-(S)-enriched-phenylpropionic acid.

6. A process as claimed in claim 4, which comprises a further salt preparation step d(vi), in which the sodium ibuprofen obtained from the salt-preparation step d(iii), is acidified in the presence of a water-immiscible solvent to produce a solution of further-(S)-enriched-ibuprofen in the water-immiscible solvent which is separated, and solid (S)-enriched-ibuprofen is then crystallised and isolated.

7. A process as claimed in claim 6, in which the water-immiscible solvent used in step d(vi) is heptane.

8. A process as claimed in claim 4, which comprises a further salt-preparation step d(vii), in which the aqueous solution of the further -(S)-enriched-sodium ibuprofen obtained from step d(iii), is acidified at an elevated temperature to give a melt which is separated from the aqueous layer and solid (S)-enriched-ibuprofen is then crystallised and isolated.

9. A process as claimed in claim 8, in which the elevated temperature is about 60° C.

10. A process as claimed in claim 1, in which the molar ratio of the substantially racemic phenylpropionic acid and the α-methylbenzylamine used in the resolution stage (a) is from 1:0.4 to 1:0.6.

11. A process as claimed in claim 1 in which, the mixture of methanol and toluene used in the resolution stage (a) comprises from about 60% to about 90% toluene by volume of the total mixture.

12. A process as claimed in claim 11, in which the mixture used in the resolution stage (a) comprises from about 70% to about 80% toluene by volume of the total mixture.

13. A process as claimed in claim 1 in which the initial temperature of the mixture used in the resolution stage (a) is in the range from about 40° C. to about 60° C.

14. A process as claimed in claim 1, in which the mixture in resolution stage (a) is cooled to a temperature in the range from about −10° C. to about 30° C.

15. A process as claimed in claim 14, in which the mixture in the resolution stage (a) is cooled to a temperature in the range from about 0° C. to about 5° C.

16. A process as claimed in claim 1, in which the mixture used in the recrystallisation stage (b) comprises from about 50% to about 80% toluene by volume of the total mixture.

17. A process as claimed in claim 16, in which the mixture used in the recrystallisation stage (b) comprises from about 60% to about 70% toluene by volume of the total mixture.

18. A process as claimed in claim 1, in which the solution in the recrystallisation stage (b) is cooled to a temperature in the range from about −10° C. to about 30° C.

19. A process as claimed in claim 18, in which the solution in the recrystallisation stage (b) is cooled to a temperature in the range from about 0° C. to about 5° C.

20. A process as claimed in claim 1, in which in the liberation stage (c), the salt of the further (S)-enriched-phenylpropionic acid obtained from the recrystallisation stage (b), is acidified with hydrochloric acid to produce an aqueous solution of (S)-α-methylbenzylamine hydrochloride, which is basified, the base being extracted into toluene and the toluene extract being reused in a subsequent resolution stage (a).

21. A process as claimed in claim 1, in which the phenylpropionic acid is ibuprofen and the desired enantiomer is the (S)-enantiomer and:
 (a) the resolution stage produces a (S)-α-methylbenzylamine salt of (S)-enriched ibuprofen of an enantiomeric purity from about 80% to about 95% by weight, and a first mother liquor comprising (R)-enriched-ibuprofen which is used in a racemisation stage (e) to produce substantially racemic ibuprofen which is introduced as part of the starting material used in a subsequent resolution stage (a);
 (b) the recrystallisation stage comprises two steps:
  (i) a first recrystallisation step comprising recrystallising the (S)-enriched-ibuprofen-(S)-α-methylbenzylamine produced from the resolution stage (a), to produce (S)-enriched-ibuprofen-(S)-α-methylbenzylamine preferably of an enantiomeric purity from about 90% to 99.9% by weight, and a second mother liquor comprising (S)-enriched-ibuprofen-(S)-α-methylbenzylamine of an enantiomeric purity from about 40% to about 70% by weight, the second mother liquor being introduced as part of the solvent used in a subsequent resolution step (a);
  (ii) a second recrystallisation step comprising recrystallising the (S)-enriched-ibuprofen-(S)-α-methylbenzylamine produced from the first recrystallisation step (b) (i), to produce substantially enantiomerically pure (S)-ibuprofen-(S)-α-methylbenzylamine, preferably of an enantiomeric purity of about 99%, and a third mother liquor comprising (S)-enriched-ibuprofen-(S)-α-methylbenzylamine of an enantiomeric purity from about 85% to about 95% by weight, the third mother liquor being introduced as part of the solvent used in a subsequent first recrystallisation step (b) (i).

22. A process as claimed in claim 21, in which the enantiomeric purity of the (S)-enriched-ibuprofen-(S)-methylbenzylamine produced from the first recrystallisation step (b)(i) is from about 94% to about 99% by weight.

23. A process as claimed in claim 21, in which the second mother liquor comprises (S)-enriched-ibuprofen-(S)-α-methylbenzylamine of an enantiomeric purity from about 40% to about 60% by weight.

24. A process as claimed in claim 21, in which the third mother liquor comprises (S)-enriched-ibuprofen-(S)-α-methylbenzylamine of an enantiomeric purity from about 88% to about 95% by weight.

25. A process as claimed in claim 1, in which the first mother liquor from the resolution stage (a) is subjected to azeotropic distillation to remove substantially all the methanol at temperatures which avoid substantial formation of by-products, the distillate being reused as part of the solvent in a subsequent resolution stage (a).

26. A process as claimed in claim 25, in which the residue remaining after the distillation of the first mother liquor is acidified to give an aqueous solution of a (S)-α-methylbenzylamine salt and an organic phase comprising (R)-enriched ibuprofen, the aqueous solution being separated and basified to give free (S)-α-methylbenzylamine which is extracted into toluene and reused as the resolving agent at the start of a subsequent resolution stage (a) along with (S)-α-methylbenzylamine recovered in the liberation stage (c); the organic phase comprising (R)-enriched-ibuprofen being racemised in a racemisation stage (e) to produce substantially racemic ibuprofen which is then introduced as part of the solvent used at the start of a subsequent resolution stage (a).

27. A process as claimed in claim 26, in which the residue remaining after distillation, is acidified with hydrochloric acid to give an aqueous solution of (S)-α-methylbenzylamine hydrochloride.

28. A process as claimed in claim 1 in which the recrystallisation stage (b) comprises three or more recrystallisation steps.

29. A process as claimed in claim 1 in which, at each stage of the process, liquors not comprising the phenylpropionic acid enriched in the desired enantiomer are recycled by using them in previous stages of the process.

\* \* \* \* \*